United States Patent [19]
Hamilton

[11] 3,959,980
[45] June 1, 1976

[54] REFRIGERANT MOISTURE DETECTION SYSTEM

[76] Inventor: Samuel L. Hamilton, 3800 NW. 22nd Ave., Miami, Fla. 33142

[22] Filed: Nov. 5, 1974

[21] Appl. No.: 521,234

Related U.S. Application Data

[63] Continuation-in-part of Ser. No. 340,373, March 12, 1973, Pat. No. 3,846,730.

[52] U.S. Cl. ............................... 62/126; 340/235; 73/336.5
[51] Int. Cl.² ........................................ F25B 49/00
[58] Field of Search ............. 62/126, 129, 150, 195; 338/34; 340/235; 73/336.5

[56] References Cited
UNITED STATES PATENTS

| | | | |
|---|---|---|---|
| 2,863,299 | 12/1958 | Ammons | 62/129 X |
| 3,059,443 | 10/1962 | Garner | 62/126 |
| 3,671,912 | 6/1972 | La Sota | 338/34 |

Primary Examiner—William E. Wayner
Attorney, Agent, or Firm—Clarence A. O'Brien; Harvey B. Jacobson

[57] ABSTRACT

A system for detecting the presence of moisture in the refrigerant of a refrigeration system and providing a signal to indicate the presence of moisture and shutdown the refrigeration system thereby avoiding damage and possible failure of the refrigeration equipment. The device is in the form of a probe or probes inserted into a flow path or flow paths of the refrigerant and an assembly for providing an audio-visual signal or alarm and shutting down the machinery prior to it becoming damaged by the moisture or water in the refrigerant.

8 Claims, 5 Drawing Figures

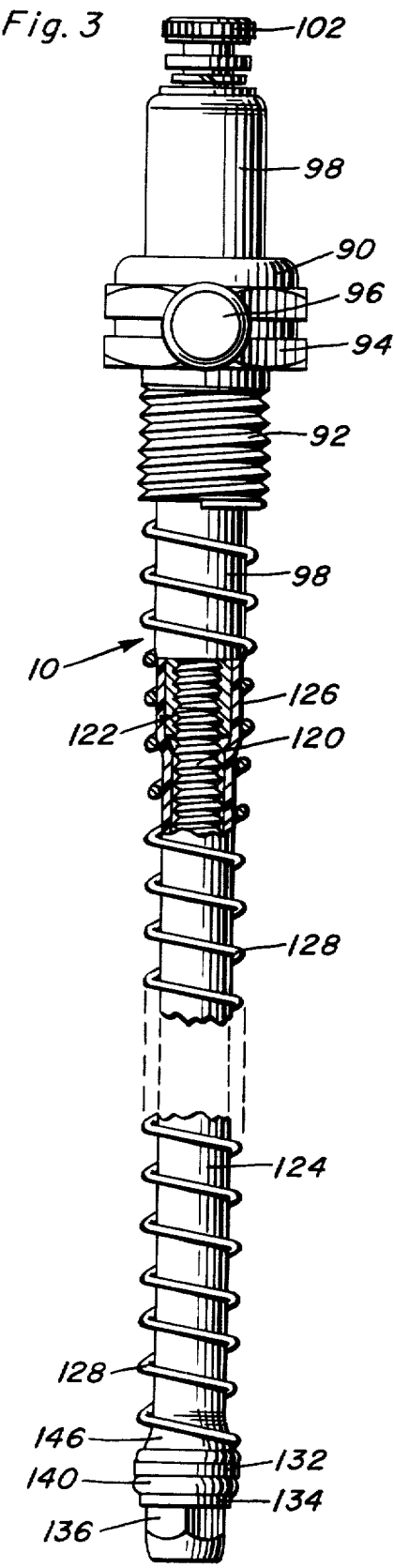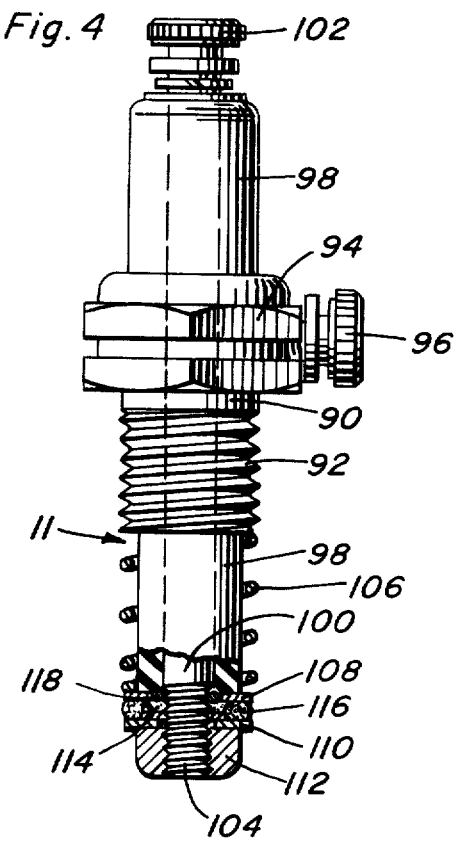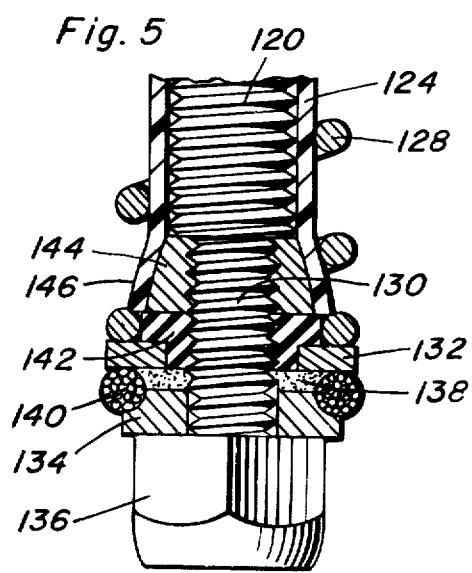

REFRIGERANT MOISTURE DETECTION SYSTEM

CROSS REFERENCE TO RELATED APPLICATION

This application is a continuation-in-part of my copending application U.S. Ser. No. 340,373, filed Mar. 12, 1973, for Proportioning Moisture Sensing Device for Refrigeration Systems, now U.S. Pat. No. 3,846,730.

BACKGROUND OF THE INVENTION

1. Field of the Invention

The present invention generally relates to a refrigerant moisture detection system and more particularly to a sensing device and control circuitry for providing an audio-visual alarm or signal when moisture is detected and shutting down the refrigeration equipment to prevent damage to such equipment by the moisture or water.

2. Description of Prior Art

One of the problems related to operation of refrigeration systems, air conditioning systems and other systems employing refrigerant is damage to such equipment caused by moisture or water in the refrigerant. Moisture in a refrigerant system causes acid formation which is destructive to the internal parts of the system. For example, hermetically sealed motors with windings exposed to the refrigerant are extremely vulnerable to water and moisture related contaminants. Such water and moisture gets into the refrigeration system through leaking gaskets, pipes, tubes, joints, mal-function of purge systems and the like and even if only a few drops of water are in the system, it will produce sufficient acid to cause major failure due to continued operation with the acid or other contaminants in the refrigerant. Additionally, under some conditions, there could be a rupture with a deluge of water which would cause major damage unless the equipment is promptly shut down. In actual operation, a high percentage of major failures of large air conditioning machines are caused by water and water related contaminants in the refrigerant. While such air conditioning equipment is fitted with various devices to protect the equipment from malfunction of its electrical and fluid flow systems, there has been no instrument available to protect the equipment from water in the refrigerant. Even if the operating engineer practices good maintenance and surveillance, he has no means of detecting the presence of a small amount of moisture generating acid nor does he have any means of detecting a sudden deluge of water in the refrigerant.

The prior patents set forth in the copending application and cited by the Patent Office therein disclose devices for moisture detection in a flow path but are not adapted for use with refrigerating or air conditioning systems in a manner that adequately detects moisture and controls operation of a signalling device and operation of the equipment.

SUMMARY OF THE INVENTION

An object of the present invention is to provide a refrigerant moisture detecting system of either a single stage type or a two-stage type and including a sensing probe for detecting the presence of moisture or moisture related contaminants in the refrigerant in a refrigeration system, operating an audio-visual alarm or signal and shutting down the equipment before damage to the system occurs.

Another object of the invention is to provide a moisture detection system in which the sensing device or probe can be of varying depth and includes an anode and cathode with desiccant crystals, pellets, powder or any other hygroscopic material disposed therebetween with pressure contact of the anode and cathode with the desiccant material and retaining and straining fabric material enclosing the periphery of the desiccant material with the electrical flow characteristics between the anode and cathode changing in response to ambient conditions in the flow path.

A further object of the invention is to provide a moisture detection system incorporating a control circuit for providing a signal to an operating engineer to indicate the presence of moisture in the refrigerant and to shut down the equipment when the presence of moisture is detected.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 3 is an elevational view of an elongated sensing probe.

FIG. 4 is an elevational view, with portions broken away illustrating a standard length probe.

FIG. 5 is an enlarged, fragmental sectional view illustrating the construction of the anode, cathode, desiccant material and related structure.

DESCRIPTION OF THE PREFERRED EMBODIMENTS

Figure 1:
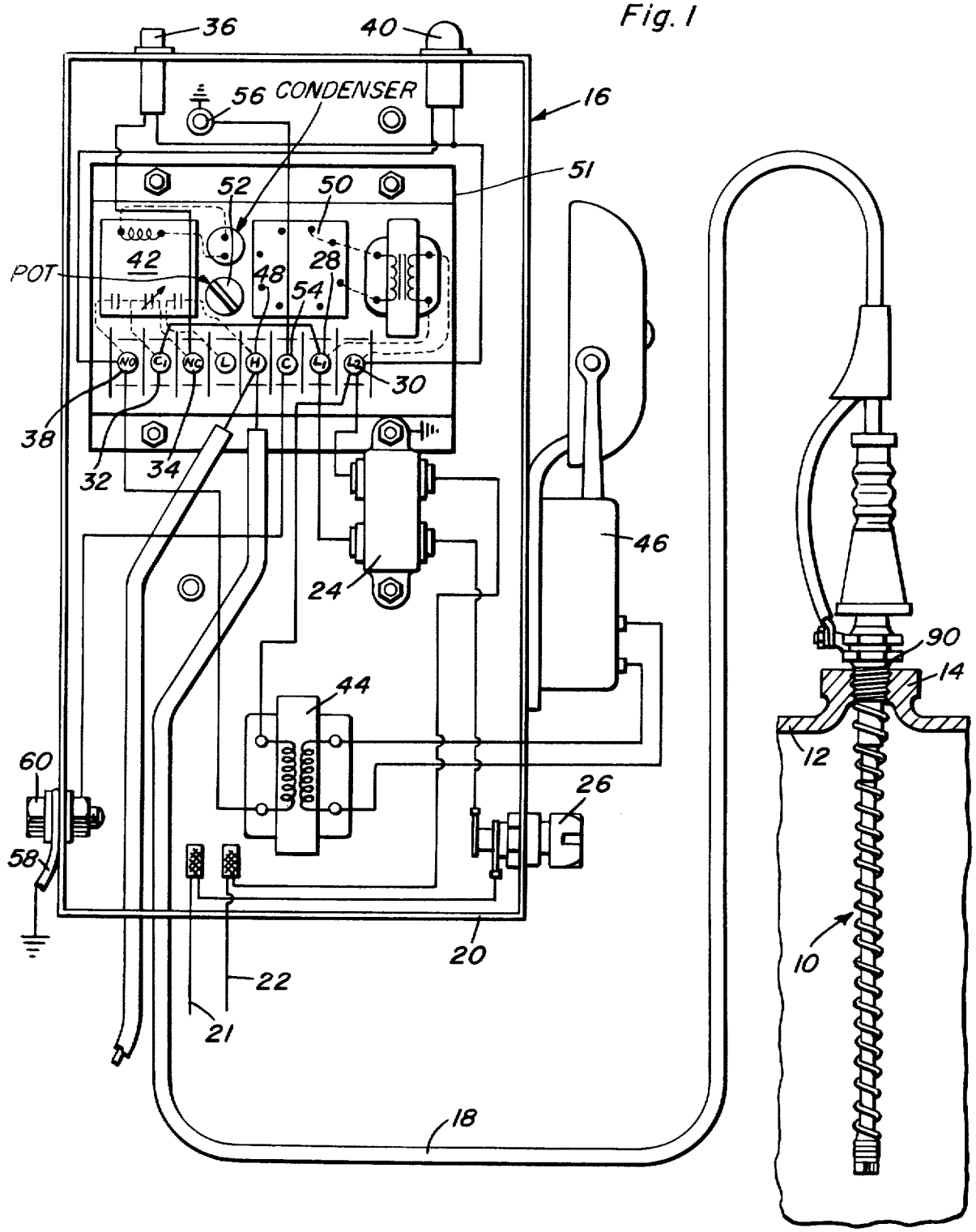
FIG. 1 is a schematic illustration of the detection system of the present invention illustrating the single stage system.
Figure 2:
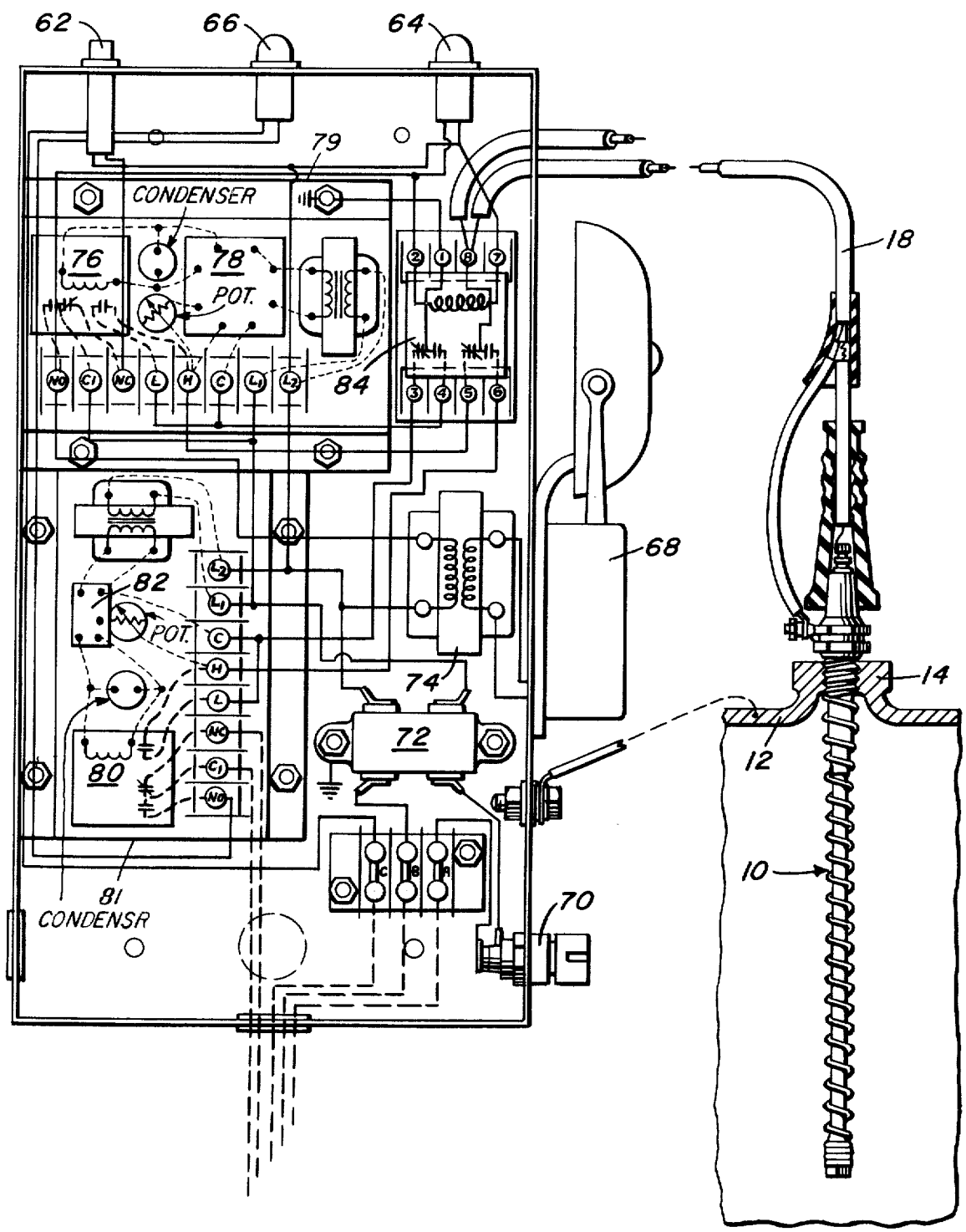
FIG. 2 is a schematic illustration of a two-stage refrigerant moisture detection and surveillance system.

FIGS. 1 and 2 illustrate schematically the association of a sensing device or probe 10 oriented in a refrigerant flow path 12 by being screwthreaded into an internally threaded adapter or member 14 which may be the branch of a T coupling or the like in the same manner as disclosed in my copending application Ser. No. 340,373, now U.S. Pat. No. 3,846,730 which structure is incorporated herein by reference thereto.

The sensing probe 10 is connected with a control device generally designated by numeral 16 through a shielded cable 18.

The control device 16 is in the form of a control box or panel 20 into which lines 21 and 22 extend which are connected to a source of electrical energy such as a conventional 120 volt circuit for supplying power to a filter 24 with the line 22 being connected directly to the filter 24 and the line 21 being connected to another terminal on the filter 24 through a fuse assembly 26 with line 21 being designated L1 and line 22 being designated L2 hereinafter. The fuse assembly 26 and the power filter 24 are conventional with the filter being grounded and the power supply lines extending to terminals 28 and 30. The hot terminal 28 is connected to terminal 32 which in turn supplies power to a normally closed switch terminal 34 which energizes a white pilot light 36 which is connected with neutral terminal 30 and neutral line 22 (L2). Also connected with the terminal 32 is a normally open switch terminal 38 that is connected to a red warning light 40 which is also connected to the neutral terminal 30 so that when the normally open switch is closed by a relay 42, the red light 40 will be actuated. The terminal 38 is also connected to one side of a transformer 44 that is also connected to the neutral terminal 30 so that when the normally open relay operated switch assembly 38 is closed, the red light 40 will be actuated and also the transformer 44 will be energized for operating a warning bell 46 which is a typical low voltage bell thus requiring the use of the transformer 44.

The shielded cable 18 which connects with the sensing probe is connected with terminal 48 so that current flow between the anode and cathode in the sensing device or probe 10 can be amplified by an amplifier 50 which includes an adjustable potentiometer 52 in the bridge circuit for operating the control relay 42. The resistance sensing amplifier 51 is a commercially available item such as the model LHS one manufactured by Curtis Development and Manufacturing Co., of Milwaukee, Wisconsin, and is a highly sensitive electronic device with a solid state plug-in amplifier 50 for operating the control relay. This is accomplished by employing a bridge circuit in the amplifier network to sense a minute alternating current flowing between the anode and cathode with the signal sensitivity being varied by a potentiometer in one leg of the bridge circuit thus providing accurate sensing with very small signal changes. When the signal produced by the probe is amplified, it will energize the red light 40, the bell 46 and the relay 42 will also open the control circuit to the refrigeration equipment thus shutting down the equipment thereby providing an effective visual warning signal, audible warning signal and shutting down the refrigeration equipment. If the relay enclosure or panel 20 is mounted on and grounded to the refrigeration machine, the terminal 54 may be grounded to a mounting bolt 56 but if the relay enclosure is remotely mounted, the enclosure is grounded to the refrigeration machine by ground wire 58 which is connected to the terminal 54 through a ground bolt 60.

FIG. 2 illustrates a similar probe 10, shielded cable 18 but in this arrangement, there is schematically illustrated a two-stage system which includes a white pilot light 62, an amber caution light 64 and a red shutdown light 66 and also a bell 68 which is energized when the light 64 is energized. This device also includes a power fuse 70 and a power filter 72 and a transformer 74 for the bell 68 all of which represent conventional structural arrangements. This arrangement includes a first stage relay 76 including a resistance sensing amplifier 78 and a second stage relay 80 and an amplifier 82 with the sensing cable or cables 18 being connected with a double pole, double throw transfer relay 84. In this arrangement, when the moisture level is relatively low and the current flow is correspondingly proportional to the moisture level, only the amber caution light and the caution bell 64 and 68 will be energized. When the moisture level increases beyond a predetermined level, the second stage amplifier and relay are energized for rendering the refrigeration machine or machines inoperative by connection to terminals C1 and NC on the second stage relay 80.

The first stage sensing amplifier system, indicated by reference numeral 79 in FIG. 2, is preferably the standard Curtis Model LHS while the second stage electronic resistance sensing amplifier of low adjustable range is preferably standard Curtis Model LCS, indicated by reference numeral 81 in FIG. 2.

As indicated, all the components are commercially available and are arranged in a compact manner within a metal or steel enclosure which may either be mounted on the refrigeration machinery itself or at a remote location in which event the box or enclosure should be grounded to the refrigeration machinery.

FIGS. 3–5 illustrate the details of construction of the probe with FIG. 3 illustrating the elongated probe 10 schematically illustrated in FIGS. 1 and 2 and FIG. 4 illustrating a shorter or standard probe designated by reference numeral 11. In each embodiment of the probe, there is provided a metallic housing 90 of stainless steel or the like which forms part of the cathode assembly and includes an externally threaded lower end portion 92 that threads into the internally threaded branch 14 and includes a polygonal portion 94 for receiving a wrench or the like to install or remove the probe. Laterally on the housing 90, there is provided a ground terminal stud and nut 96. Internally of the housing 90, a porcelain insulator 98 is provided which extends both above and below the housing 90 and anchored to the housing 90 in the manner of a spark plug. Extending through the insulator 98 is a metal rod in the form of an anode 100 having a terminal stud and nut 102 at the upper end. The lower end of the anode 100 is externally threaded as indicated by numeral 104 and projects below the lower end of the insulator 98. To the extent described above, the probes 10 and 11 are identical. When the standard probe is used as in FIG. 4, a short stainless steel spring 106 is provided in encircling relation to the lower end of the insulator 98 with one end abutting the bottom end of the housing 90. Positioned on the lower threaded end 104 of the anode 100 is a cathode stainless steel disk 108, an anode stainless steel disk 110 and a threaded locknut 112. Positioned between the disks 108 and 110 is desiccant material 114 and a fabric retaining and straining ring 116 which structure is substantially the same as that disclosed in my copending application with the lower end of the spring engaging the disk 108 with both the spring and the disk 108 being insulated from the anode 104 by the use of a resilient insulating grommet 118. Thus, as the desiccant material absorbs moisture in the flow path, the electrical flow characteristics between the anode and cathode will vary with such change in resistance being amplified with the resultant signal controlling the signal lights, audio-signal and the control circuit to the refrigeration equipment.

When it is desired to use a longer probe, the probe structure illustrated in FIGS. 3 and 5 will be used and in this construction, an elongated threaded rod anode 120 will be joined to the threaded lower end 104 of the anode 100 by a sleeve which is internally threaded and designated by numeral 122. Positioned over the rod 120 and the sleeve 122 is an insulating tube 124 of plastic material with the upper end thereof being expanded as at 126 to cover the threaded sleeve coupling 122 and to insulate the anode 120 from the elongated spring 128 which abuts the housing 90 in the same manner as in FIG. 4. At the lower end of the probe in FIG. 3, the rod 120 which is externally threaded at 130 is provided with a cathode disk 132 engaged by the lower convolution of the spring and a disk 134 in the form of an anode disk engaging the rod 120 and retained in position by a locknut 136. Positioned between the cathode disk and anode disk is desiccant material 138 and a fabric straining and retaining ring 140. The cathode disk 132 and the lower convolution of the spring 128 are electrically insulated from the anode by an insulating grommet 142. A tapered nut 144 is engaged with the inner end portion of the threaded lower end 130 of the rod 120 and extends into the insulating tube 124 and causes the lower end of the insulating tube 124 to be expanded as designated by numeral 146 which securely locks the insulating tube in relation to the anode rod with the insulating grommet 142 also engaging the nut 144. This assembly operates in the same manner as the structure in FIG. 4 and in the same manner as the structure disclosed in my copending application.

With the construction illustrated in FIGS. 3 and 5, the anode rod and tube may be cut to a desired length and springs of varying lengths may be used in order to enable the length of the probe to be varied so that the sensing device may be positioned properly in relation to the flow path. The pressure exerted by the spring which also serves as the cathode against the cathode disk serves to exert pressure on the desiccant material and the fabric ring to assure proper contact between the components so that a proper electrical flow path will be provided between the anode and cathode so that resistance to such flow and the change in such resistance may be sensed and amplified for providing an audio-visual signal or warning and a device for shutting down the equipment prior to damage.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. A refrigerant moisture detection system comprising a visual signal means, an audio signal means and a sensing device positionable in a refrigerant flow path for detecting the presence of absorbed moisture and moisture related contaminants in the refrigerant, said sensing device including an anode and cathode disposed in spaced relation in the flow path and electrically connected to a source of electrical energy, absorbent means disposed between the anode and cathode and in the flow path with the absorbent means including material capable of change of electrical conductivity in response to moisture absorption, amplifier means and relay means electrically connected with the sensing device to sense the change in electric current flow through the sensing device to produce a signal and amplify the signal to operate a relay for energizing the visual signal means and audio signal means and shut down the refrigeration equipment prior to damage.

2. The structure as defined in claim 1 wherein said visual signal means includes a two stage light including a caution light and a red light, said means sensing change in electrical flow characteristics of the sensing device including means energizing the caution light when the moisture detected is at a relatively low level and energizing the red light and shutting down the refrigeration equipment when the moisture detected exceeds a predetermined level.

3. A refrigerant moisture detection system comprising a visual signal means, an audio signal means and a sensing device positionable in a refrigerant flow path for detecting the presence of absorbed moisture and moisture related contaminants in the refrigerant, said sensing device including an anode and cathode disposed in spaced relation in the flow path and electrically connected to a source of electrical energy, absorbent means disposed between the anode and cathode and in the flow path with the absorbent means including material capable of change of electrical conductivity in response to moisture absorption, amplifier means and relay means electrically connected with the sensing device to sense the change in electric current flow through the sensing device to produce a signal and amplify the signal to operate a relay for energizing the visual signal means and audio signal means and shut down the refrigeration equipment prior to damage, said sensing device including an elongated rod forming the anode, said cathode including a housing attached to a refrigerant flow line, a conductive spring encircling the housing and coextensive with the anode but insulated therefrom a cathode disc engaged by the spring, an anode disc attached to the anode rod in spaced relation to the cathode disc, said absorbent means being in the form of desiccant material between the discs with the spring biasing the discs into pressure contact with the desiccant material, and a fabric retaining member encircling the desiccant material and disposed between the discs for retaining the desiccant material between the discs and straining moisture or moisture related contaminants absorbed by the desiccant material.

4. The structure as defined in claim 3 wherein said anode rod is sectional to enable variation in length, an insulating tube enclosing the anode rod, an expanding nut on the anode rod adjacent the cathode disc and having a tapered external surface for expanding the insulating tube for locking the assembly together, a grommet of insulating material positioned between the expanding nut, cathode disc and anode rod for isolating the cathode spring and disc from the anode and expanding nut.

5. The structure as defined in claim 4 wherein the sectional anode rod is interconnected by a threaded coupling, said insulating tube also enclosing the threaded coupling.

6. A refrigerant moisture detection system comprising a signal and a sensing device positionable in a refrigerant flow path for detecting the presence of moisture and moisture related contaminants in the refrigerant, said sensing device including an anode and cathode disposed in spaced relation in the flow path and electrically connected to a source of electrical energy, absorbent means disposed between the anode and cathode and in the flow path with the absorbent means including material capable of change of electrical conductivity in response to moisture absorption, amplifier means and relay means electrically connected with the sensing device to sense the change in electric current flow through the sensing device to produce a signal and amplify the signal to operate a relay for energizing the signal means and shut down the refrigeration equipment prior to damage, said sensing device including an elongated rod forming the anode, said cathode including a housing attached to a refrigerant flow line, a conductive spring encircling the housing and coextensive with the anode but insulated therefrom, a cathode disc engaged by the spring, and anode disc attached to the anode rod in spaced relation to the cathode disc, said absorbent means being in the form of desiccant material between the discs with the spring biasing the discs into pressure contact with the desiccant material, and a fabric retaining member encircling the desiccant material and disposed between the discs for retaining the disiccant material between the disc and straining moisture or moisture related contaminants absorbed by the desiccant material.

7. The structure as defined in claim 6 wherein said anode rod is sectional to enable variation in length, an insulating tube enclosing the anode rod, an expanding nut on the anode rod adjacent the cathode disc and having a tapered external surface for expanding the insulating tube for locking the assembly together, a grommet of insulating material positioned between the expanding nut, cathode disc and anode rod for isolating the cathode spring and disc from the anode and expanding nut.

8. The structure as defined in claim 3 wherein said visual signal means includes a three-stage light including a caution light and a red light, said means sensing change to electrical flow characteristics of the sensing device including means energizing the caution light when the moisture detected is at a relatively low level and energizing the red light and shutting down the refrigeration equipment when the moisture detected exceeds a predetermined level.

* * * * *